United States Patent [19]

Erekson et al.

[11] Patent Number: 4,950,827

[45] Date of Patent: * Aug. 21, 1990

[54] OXIDATIVE COUPLING OF ALIPHATIC AND ALICYCLIC HYDROCARBONS WITH ALIPHATIC AND ALICYCLIC SUBSTITUTED AROMATIC HYDROCARBONS

[75] Inventors: Erek J. Erekson, LaGrange; Anthony L. Lee, Glen Ellyn, both of Ill.

[73] Assignee: Institute of Gas Technology, Chicago, Ill.

[*] Notice: The portion of the term of this patent subsequent to Jun. 19, 2007 has been disclaimed.

[21] Appl. No.: 274,454

[22] Filed: Nov. 21, 1988

Related U.S. Application Data

[63] Continuation-in-part of Ser. No. 172,808, Mar. 28, 1988, Pat. No. 4,826,796.

[51] Int. Cl.$^5$ ................................ C07C 2/00
[52] U.S. Cl. ..................... 585/415; 585/500; 585/541; 585/654; 585/700; 585/921; 585/926; 585/943
[58] Field of Search ............ 585/943, 500, 428, 636, 585/541, 921, 926, 415, 417

[56] References Cited

U.S. PATENT DOCUMENTS

| | | | |
|---|---|---|---|
| 3,728,410 | 4/1973 | Hughes | 585/428 |
| 3,751,506 | 8/1973 | Burress | 585/454 |
| 3,849,292 | 11/1974 | Gleim | 208/111 |
| 4,107,224 | 8/1978 | Dwyer | 585/449 |
| 4,443,644 | 4/1984 | Jones et al. | 585/500 |
| 4,443,645 | 4/1984 | Jones et al. | 585/500 |
| 4,443,646 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,444,984 | 4/1984 | Jones et al. | 585/500 |
| 4,463,204 | 7/1984 | Liu | 585/438 |
| 4,499,322 | 2/1985 | Jones et al. | 585/500 |
| 4,499,323 | 2/1985 | Gaffney | 585/500 |
| 4,499,324 | 2/1985 | Gaffney | 502/324 |
| 4,523,049 | 6/1985 | Jones et al. | 585/500 |
| 4,571,443 | 2/1986 | DiCosimo et al. | 585/428 |
| 4,656,155 | 4/1987 | Josefowicz | 585/500 |
| 4,704,487 | 11/1987 | Devries et al. | 585/417 |
| 4,704,488 | 11/1987 | Devries et al. | 585/415 |
| 4,704,493 | 11/1987 | Devries et al. | 585/415 |
| 4,826,796 | 5/1989 | Erekson et al. | 502/202 |

FOREIGN PATENT DOCUMENTS

| | | |
|---|---|---|
| 0112754 | 7/1984 | European Pat. Off. |
| 0177327 | 4/1986 | European Pat. Off. |
| 0183225 | 6/1986 | European Pat. Off. |
| 2104462 | 4/1972 | France |

OTHER PUBLICATIONS

Keller, G. E. and M. M. Bhasin, J. of Catalysis 73, 9–19 (1982).
Hinsen, W. and M. Baerns, Chem.-Ztg., 107, 223–226 (1983).
Hinsen, W., W. Bytyn and M. Baerns, Proc. 8th Int. Congr. Catal., Berlin, III 581–592 (1984).
Kimble, James B. and John H. Kolts "Oxidative Coupling of Methane to Higher Hydrocarbons", Energy Progress, vol. 6, p. 227 (1986).
Driscol, D. J., W. M. Martir, J. Wang and J. H. Lunsford, J. Am. Chem. Soc. 107, 58–63 (1985).
Ito, T., J. Wang, C. Lin and J. H. Lunsford, J. Am. Chem. Soc. 107, 5062–5064 (1985).
Illingworth, G. F. and G. W. Lester, ACS Petroleum Division Preprints, 12, No. 3, 161 (1967).
Lee, K. W., M. J. Choi, S. B. Kim and C. S. Choi, Ind. Eng. Chem. Res. 26, 1951 (1987).
Kegeyan, E. M., I. S. Vardanyan and A. B. Nalbandyan, Kinetics and Catalysis 17, No. 4, 749–754 and No. 4,755,759 (1976).
Kirk-Othmer, Encyclopedia of Chemical technology, Third Edition, vol. 21, Styrene, pp. 770–801.
Chemical Abstracts: (USSR) 97:127153K (1982); 99:70137t (1983); 101:74734t (1984) and 101:38205n (1984).

*Primary Examiner*—A. Pal
*Attorney, Agent, or Firm*—Thomas W. Speckman

[57] ABSTRACT

A catalyst and a process for oxidative coupling of aliphatic and alicyclic hydrocarbon compounds with aliphatic and alicyclic substituted aromatic hydrocarbon compounds to form a longer substituent hydrocarbon on the aromatic ring. The catalyst is mixed basic metal oxide catalyst, one preferred catalyst is boron/alkali metal promoted metal oxide. Reaction of methane with toluene and oxygen according to this invention results in conversion to styrene.

35 Claims, No Drawings

OXIDATIVE COUPLING OF ALIPHATIC AND ALICYCLIC HYDROCARBONS WITH ALIPHATIC AND ALICYCLIC SUBSTITUTED AROMATIC HYDROCARBONS

CROSS-REFERENCE TO RELATED APPLICATION

This application is a continuation-in-part of copending U.S. Patent Application Ser. No. 172,808, filed Mar. 28, 1988, now U.S. Pat. No. 4,826,796.

BACKGROUND OF THE INVENTION

1. Field of the Invention

This invention relates to a process using mixed basic metal oxide catalysts for production of higher hydrocarbons by oxidative coupling of aliphatic and alicyclic hydrocarbon compounds with aliphatic and alicyclic substituted aromatic hydrocarbon compounds to form a longer substituent hydrocarbon on the aromatic ring. Reaction of methane with toluene and oxygen in the presence of a mixed basic metal oxide catalyst according to this invention results in high conversion to form styrene.

2. Description of the Prior Art

Methane is currently available in large quantities from natural gas, anaerobic digestion of organic material, and chemical processing sources. However, use of methane as a chemical feedstock has been limited due to its high stability. It has been highly desirable to develop a catalyst for such reactions to enable operation under milder conditions with greater control over thermodynamic and kinetic processes as well as provide product selectivity and high reaction rate.

Oxidative coupling of methane to form higher hydrocarbons has been shown to be effected over a number of metal oxides, but yields of desired products have been low, as discussed by Keller, G. E. and M. M. Bhasin, J. of Catalysis 73, 9-19 (1982). Sodium and lead on alumina has been found to catalyze the formation of ethane and ethylene from methane, as disclosed in Hinsen, W. and M. Baerns, Chem.-Ztg., 107, 223-226 (1983) and Hinsen, W., W. Bytyn and M. Baerns, Proc. 8th Int. Congr. Catal., Berlin, III 581-592 (1984). Several U.S. patents teach a series of supported metal oxides which while effective for the conversion of methane to ethane and ethylene, are based on reducible metal oxides and used in a stoichiometric fashion by alternately exposing them to an oxidizing atmosphere and then to methane in the absence of oxygen. U.S. Pat. Nos. 4,443,644; 4,443,645; 4,443,646; 4,443,647; 4,443,648; 4,443,649; 4,444,984, 4,499,322; 4,499,323; and 4,499,324; and 4,523,049.

Later work has demonstrated that magnesium oxide and calcium oxide, when promoted with alkali metal salts, are active for oxidative coupling of methane to ethane and ethylene in the presence of oxygen. See Kimble, James B. and John H. Kolts, "Oxidative Coupling of Methane to Higher Hydrocarbons", Energy Progress, Vol. 6, p. 227 (1986); Driscoll, D. J., W. M. Martir, J. Wang and J. H. Lunsford, J. Am. Chem. Soc. 107, 58-63 (1985); and Ito, T., J. Wang, C. Lin and J. H. Lunsford, J. Am. Chem. Soc. 107, 5062-64 (1985). These later catalysts have the advantage of operating continuously, not requiring regeneration or pretreatment.

Borates and boron compounds have been used in partial oxidation of hydrocarbons, such as boric acid to oxidize long chain normal paraffins in the liquid phase (Illingworth, G. F. and G. W. Lester, ACS Petroleum Division Preprints, 12, No. 3, 161 (1967)) and oxidation of n-dodecane in the liquid phase to the corresponding alcohol (Lee, K. W., M. J. Choi, S. B. Kim and C. S. Choi, Ind. Eng. Chem. Res. 26, 1951 (1987)). Boric acid has been used by coating reactor walls in the combustion of methane to eliminate free radical destruction at temperatures of less than 513° C. (Kegeyan, E. M., I. S. Vardanyan and A. B. Nalbandyan, Kinetics and Catalysis 17, No. 4,749-754 and No. 4,755-759 (1976))

A review of styrene synthesis processes is given in Kirk-Othmer, Encyclopedia of Chemical Technology, Third Edition, Vol. 21, Styrene, pgs. 770-801.

Vapor phase alkylation of aromatic hydrocarbons in the presence of a crystalline aluminosilicate zeolite catalyst is taught by U.S. Pat. Nos. 4,107,224 and 3,751,506.

A number of publications describe oxidative methylation of toluene performed in Russia: Chemical Abstracts 97:127153K (1982) teaches non-catalytic methylation of toluene depended mostly on pressure and PhMe/0/CH$_4$ molar ratio; Chemical Abstracts 99:70137t (1983) teaches oxidative methylation of toluene using a Ni-V oxide or V oxide catalyst; Chemical Abstracts 101:74734t (1984) teaches oxidative methylation of toluene in presence of 0 (max. 15 percent in reaction mixture) results in products including styrene; Chemical Abstracts 101:38205 n (1984) teaches simultaneous production of styrene, ethylbenzene, benzene, and phenols by reaction of toluene with $C_{1-4}$ alkanes in the presence of 0 and Fe$_2$O$_3$ or TiO$_2$ at 600°-800°. Productivity increased at higher pressure in presence of H$_2$O$_2$ and/or (Me$_3$C)$_2$O$_2$ and U.S. Pat. No. 3,830,853 teaches reaction of toluene with a lower paraffin hydrocarbon in the presence of oxygen at 600°-900° C. and space velocity of 2000-10000 hour$^{-1}$.

SUMMARY OF THE INVENTION

This invention provides a catalytic process for oxidative coupling of aliphatic and alicyclic hydrocarbon compounds with aliphatic and alicyclic substituted aromatic hydrocarbon compounds to produce a longer substituent hydrocarbon on the aromatic ring. The catalyst used in the process of this invention is fully described in our copending U.S. Patent Application, Ser. No. 172,808. Oxidative coupling of methane using the same catalyst is fully described in U.S. Patent Application Ser. No. 07/274,415, filed 11/21/1988, and dehydrogenation of saturated hydrocarbon chains using the same catalyst is fully described in U.S. Patent Application Ser. No. 07/274,499, filed 11/21/88. The reaction of an aliphatic or alicyclic hydrocarbon compound with an aliphatic or alicyclic substituted aromatic hydrocarbon compound and oxygen is conducted in the presence of a mixed basic metal oxide catalyst at elevated temperature according to the following general reaction:

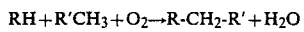

wherein R is an aliphatic or alicyclic hydrocarbon radical; and

R' is an aliphatic or alicyclic hydrocarbon radical substituted on an aromatic hydrocarbon ring.

The mixed basic metal oxide catalyst used in the process of this invention has the formula:

xA.yB.zC.qO wherein
- A is an alkali metal selected from lithium, sodium, potassium, rubidium, cesium and mixtures thereof;
- B is a cation which has an ionization state 1 greater than the ionization state of C;
- B is selected from scandium, yttrium, lanthanum, actinium, aluminum, boron and mixtures thereof from Group IIIA and IIIB of the Periodic Table, preferably boron, aluminum, yttrium, and lanthanum when C is selected from beryllium, magnesium, calcium, strontium, barium, radium, zinc, cadmium, mercury and mixtures thereof from Group IIA and IIB of the Periodic Table, preferably magnesium, calcium, barium and zinc, and
- B is selected from titanium, zirconium, hafnium, silicon and mixtures thereof from Group IVA and IVB of the periodic Table when C is selected from scandium, yttrium, lanthanum, actinium, aluminum, boron and mixtures thereof from Group IIIA and IIIB of the Periodic Table, preferably boron, aluminum, yttrium and lanthanum;
- x and y are in the mole fractions of z such that when z=1 then x=0.001 to 0.25, preferably 0.05 to 0.15 and y=0.001 to 0.25, preferably 0.002 to 0.20; and
- q is a number necessary to maintain charge balance with 0 being oxygen.

In a preferred embodiment, a boron/alkali metal promoted metal oxide catalyst having boron in amounts of about 0.2 to about 20 mole percent (about 0.05 to about 5.0 weight percent), alkali metal promoter selected from the group consisting of lithium, sodium and potassium in amounts of about 0.1 to about 25 mole percent (about 0.1 to about 40 weight percent), metal oxide selected from the group consisting of magnesium oxide, calcium oxide, zinc oxide, and barium oxide are suitable for the catalytic oxidative coupling process according to this invention.

DESCRIPTION OF PREFERRED EMBODIMENTS

The process of this invention provides a longer hydrocarbon substituent on an aromatic ring by gas phase oxidative coupling of saturated carbon atoms of an aliphatic or alicyclic hydrocarbon compound with an aliphatic or alicyclic substituted aromatic hydrocarbon and oxygen in the presence of a mixed basic metal oxide catalyst, such as a boron/alkali metal promoted metal oxide catalyst.

Suitable aliphatic and alicyclic hydrocarbon compounds for use as feedstocks in the process of this invention include straight and branched chain saturated and unsaturated aliphatic hydrocarbons, such as methane, ethane, propane, butane, heptane, pentane, hexane, octane, isobutane, isohexane, isooctane, 1-pentene, 1-hexene and mixtures thereof; cyclic chain saturated and unsaturated alicyclic hydrocarbons, such as cyclobutane, cycloheptane, cycloheptene, cyclohexane, cyclohexene and mixtures thereof; and aryl substituted aliphatic and alicyclic hydrocarbons, such as toluene, xylene, mesitylene, durene, cumene and mixtures thereof. In the case of unsaturated hydrocarbons, it should be noted that the oxidative coupling of this invention does not occur at the unsaturated bonding. Suitable aliphatic and alicyclic substituted aromatic hydrocarbon compounds for use as feedstocks in this invention are aromatic ring hydrocarbons having at least one aliphatic or alicyclic hydrocarbon radical substituent on the aromatic ring, such as toluene, xylene, indan, tetralin, and mixtures thereof.

The reactions are fed to the reaction zone in mole percent proportions of about 50 to about 90 mole percent aliphatic or alicyclic hydrocarbon compounds, preferably about 75 to about 85 mole percent; about 2 to about 40 mole percent substituted aromatic hydrocarbon, preferably about 5 to about 15 mole percent; and about 2 to about 20 mole percent oxygen, preferably about 5 to about 12 mole percent. Steam may be added in an amount of up to about 1 mole of steam per mole hydrocarbon to inhibit deep oxidation. Steam does not enter into the reaction but solely acts as an oxidation inhibitor.

An important aliphatic feedstock suitable for use in the process of this invention may comprise any methane containing gas which does not contain interfering compounds. Preferably, the methane containing gas used in the process of this invention comprises about 25 mole percent up to about 100 mole percent methane. Suitable sources of methane containing gas include natural gas, synthetic natural gas (SNG), product gas from gasification of carbonaceous materials, such as gasification of coal, peat, shale, and the like, as well as products of anaerobic digestion of various biomass materials. These gases principally comprise methane and may contain other hydrocarbon gases such as ethane and propane which may produce corresponding chemical reactions to those of methane in the process of this invention. Purification of such mixed gases comprising principally methane is not usually necessary. These sources of methane containing gas and processes for producing methane are well known in the art.

Important substituted aromatic feedstocks include toluene and xylene available from commercial sources.

Any oxygen containing gas not containing interfering chemical compounds are useful as a feedstock in this invention. The term "oxygen containing gas" as used throughout this disclosure and claims, refers to gas containing oxygen, such as air and gases having an oxygen content of up to 100 percent. It is preferred to use oxygen containing gas comprising over 50 volume percent oxygen. The amounts of oxygen used in the process of this invention is expressed as pure oxygen. The oxygen containing gas may be preheated by thermal exchange with the catalyst bed to a temperature suitable for the reaction controlling step of the process.

The catalyst used in the catalytic process for oxidative coupling according to this invention is a mixed basic metal oxide catalyst having the formula xA.yB.zC.qO wherein A, B, C, x, y, z and q have the meanings set forth above with 0 being oxygen. The catalysts used in the process of this invention have only one oxidation state besides the metal, that is Ti, Zr, Hf and Si are only +4 and B, Al, Y and La are only +3, while Mg, Ca, Sr and Ba are only +2 and Li, K, Na, Rb and Cs are only +1. In a particularly preferred embodiment, the catalyst of this invention is a boron/alkali metal promoted metal oxide catalyst having boron in amounts of about 0.2 to about 20 mole percent (about 0.05 to about 5 weight percent) and preferably about 0.4 to about 2 mole percent (about 0.1 to about 0.5 weight percent); alkali metal promoter selected from the group consisting of lithium, sodium and potassium in amounts of about 0.1 to about 25 mole percent (about 0.1 to about 40 weight percent) and preferably about 0.5 to about 8 mole percent (about 0.5 to about 2.0 weight percent)

and the remainder metal oxide selected from the group consisting of magnesium oxide, calcium oxide, zinc oxide, and barium oxide. A preferred catalyst is boron/lithium promoted magnesium oxide having about 0.20 to about 0.30 weight percent boron and about 0.8 to about 1.2 weight percent lithium.

The catalyst for use in this invention may be prepared by mixing water soluble ions and/or compounds of elements set forth as alkali metal (A) and cation (B) to obtain complete solution of the solids. A wide variety of non-interfering ions may be used to form suitable water soluble compounds as long as they do not cause undesired chemical interference. Suitable such compounds include acids, oxides, hydrides, and nitrates, carbonates, hydroxides, respectively. The aqueous solution of (A) and (B) are added to metal oxide (C) powder and well mixed followed by drying at a sufficient temperature and for a sufficient time to expel volatile components. The mixture is then crushed and sieved to a small size for catalytic use. Conventional and well known catalyst manufacturing techniques may be employed to produce the catalyst material noted above. When preparing these catalytic materials, it is preferred to employ manufacturing techniques resulting in a product having a substantially uniform or homogeneous composition. Shaping of the material may be effected according to conventional techniques of the art, particularly tableting, or pelleting or extrusion. The catalyst may be used unsupported or alternatively it may be supported on an inert support as known to the art, such as alumina, silica, activated carbon and the like.

A preferred catalyst may be prepared by mixing a water soluble compound of boron, such as boric acid, boron oxides, borohydrides, and a water soluble salt of the alkali metal promoter, such as nitrate, carbonate, hydroxide or water soluble ion to obtain complete solution of the solids. The aqueous solution of boron and alkali metal is added to the metal oxide powder with stirring to obtain a homogeneous mixture which may then be dried at a temperature in excess of about 110° C. The dried mixture may then be calcined at a temperature of 700° to 750° C. for a sufficient time to expel volatile portions. The mixture is then crushed and sieved to an appropriately small mesh size of about −6 to about +40, preferably about −12 to about +20 for use as a catalyst.

The catalyst may be placed into a reactor, such as a tube-shell fixed bed, fluidized bed, moving bed, or interbed heat exchange type, Fischer-Tropsch type, or other reactor type known to the art. The oxidative coupling process according to this invention is carried out by passing the gaseous aliphatic or alicyclic hydrocarbon and aromatic feedstocks and oxygen over the mixed basic metal oxide catalyst as defined above at about 300° to about 1100° C., preferably about 600° to about 900° C. Suitable gas residence times are about 0.002 to about 0.00002 hour preferably about 0.0005 to about 0.0001 hour with space velocity of about 500 to about 50,000 vol/vol/hr, preferably about 1000 to about 5000 vol/vol/hr. The reaction may be carried out at about pressures of about 1 to about 1515 psia, preferably about 1 to about 150 psia, pressures above atmospheric may enhance the rate of reaction. Suitable reactor vessels for use at the above operating temperatures and pressures are well known to the art. The products of the single reactor used in the process of this invention may be passed to a simple separator for separation of the hydrocarbon product, condensate, and vent gas.

One important oxidative coupling reaction according to the process of this invention is the production of styrene directly by coupling of toluene and methane by the following reaction in the presence of the above defined catalyst:

$$C_6H_5CH_3 + CH_4 + O_2 \rightarrow C_6H_5C_2H_3 + 2H_2O$$

At 750° C. the heat of reaction ($\Delta H$) is −73 kcal/mole and the sensible heat plus the heat of vaporization of toluene is about 55 kcal/mole. Thus the process operates close to autothermal conditions after initial light-off. Conventional processes using $Fe_2O_3$ as a catalyst with $Cr_2O_3$ as a stabilizer and $K_2CO_3$ as a coke retardant for production of styrene require ethylbenzene feedstock, produced from expensive benzene and ethylene and require large amounts of superheated steam (800° C. and molar ratio 14 steam to 1 ethylbenzene) due to the conversion of ethylbenzene to styrene being endothermio. The process of this invention uses relatively inexpensive toluene, methane and air as feedstock to a single reactor where both styrene and ethylbenzene are produced in a process that does not require superheated steam.

The specific examples are intended to be illustrative only and are not intended to limit the invention in any way.

EXAMPLE I

A mixture of 3.07 grams Fisher Certified lithium nitrate and 0.43 gram Aesar 99.99 percent pure boric acid was added to a beaker. Deionized water, 50ml, was added to the beaker and stirred to obtain complete solution of the solids in the water. The aqueous solution of lithium nitrate and boric acid was slowly added to 30.0 grams alpha magnesium oxide powder and stirred to obtain a homogeneous preparation which was then dried overnight at 118° C. The composition of the mixture was 1.0 weight percent elemental lithium and 0.24 weight percent elemental boron. The mixture was then calcined for 15 minutes at 700° C. and crushed and sieved to −12+20 mesh. Chemical analysis after calcining showed 0.97 weight percent elemental lithium and 0.17 weight percent elemental boron. Surface area of the product was 2.0 meters$^2$/gram. The product was then used as a catalyst in accordance with Example X following which analysis showed 0.94 weight percent lithium, 0.20 weight percent boron, and surface area of 1.5 meters2/gram.

EXAMPLE II

In a manner similar to Example I an aluminum/lithium promoted magnesium oxide catalyst was formed by adding 3.08 grams of Fisher Certified lithium nitrate and 2.63 grams of Fisher Certified aluminum nitrate to a beaker. Deionized water, 50 ml, was added to the beaker and stirred to obtain complete solution of the solids in the water. The aqueous solution of lithium nitrate and aluminum nitrate was slowly added to 30.0 grams of alpha magnesium oxide powder and stirred to obtain a homogeneous preparation which was then dried overnight at 118° C. The composition of the mixture was 1.0 weight percent elemental lithium and 0.6 weight percent elemental aluminum. The mixture was then calcined for 15 minutes at 700° C. and crushed and sieved to −12+20 mesh.

EXAMPLE III

In a manner similar to Example I a boron/lanthanum/lithium promoted magnesium oxide catalyst was formed by adding 3.07 grams of Fisher Certified lithium nitrate, 3.03 grams of Alpha lanthanum nitrate hexahydrate and 0.57 gram of boric acid (Aesar 99.99 percent pure) to a beaker. Deionized water, 50 ml, was added to the beaker and stirred to obtain complete solution of the solids in the water. The aqueous solution of lithium nitrate, lanthanum nitrate and boric acid was slowly added to 30.0 grams of Alpha (−325 mesh) magnesium oxide powder and stirred to obtain a homogeneous preparation which was then dried overnight at 115° C. The composition of the mixture was 1.0 weight percent elemental lithium, 3.2 weight percent elemental lantanum and 0.35 weight percent elemental boron. The mixture was then calcined for 15 minutes at 700° C. and crushed and sieved to −12+20 mesh.

EXAMPLE IV

Gaseous feedstock was fed to a tubular reactor containing a packed bed of $0.06Li:0.009La:0.012B:1.0MgO$ catalyst prepared as set forth in Example III. The feedstock comprised methane/air/toluene in proportions of 60/40/5 mole fraction. A single pass was made at 3000 SCF/h-ft$^3$, atmospheric pressure, and 665° C. resulting in a product isolated in an ice trap and analyzed as follows:

|  | Weight percent |
| --- | --- |
| Toluene | 78.3 |
| Benzene | 1.4 |
| Ethyl benzene | 8.5 |
| Styrene | 4.4 |
| Xylenes | 0.9 |
| Propyl benzene | 1.0 |
| Diphenyl ethane | 1.7 |
| Other aromatics | 3.8 |

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A process for producing higher molecular weight hydrocarbons by forming longer substituent hydrocarbon on an aromatic ring, said process comprising:

oxidative coupling a compound selected from aliphatic hydrocarbon compounds, alicyclic hydrocarbon compounds, and mixtures thereof with a compound selected from aliphatic substituted aromatic hydrocarbon compounds, alicyclic substituted aromatic hydrocarbon compounds, and mixtures thereof to form a longer substituent hydrocarbon on an aromatic ring in the presence of oxygen and a mixed basic metal oxide catalyst having the formula:

$$xA.yB.zC. qO$$

wherein

A is an alkali metal selected from lithium, sodium, potassium, rubidium, cesium and mixtures thereof;

B is action which has an ionization state 1 greater than the ionization state of C;

B is selected from the group consisting of scandium, yttrium, lanthanum, actinium, aluminum, boron and mixtures when C is selected from the group consisting of beryllium, magnesium, calcium, strontium, barium, radium, zinc, cadmium, mercury and mixtures thereof, and B is selected from the group consisting of titanium, zirconium, hafnium, silicon and mixtures thereof, when C is selected from the group consisting of scandium, yttrium, lanthanum, actinium, aluminum, boron and mixtures thereof;

x and y are in mole fractions of z such that when z=1 then x=0.001 to 0.25, and y=0.001 to 0.25; and q is a number necessary to maintain charge balance with O being oxygen.

2. A process according to claim 1 wherein said aliphatic and alicyclic hydrocarbon compounds are selected from straight and branched chain saturated and unsaturated aliphatic hydrocarbons, cyclic chain saturated and unsaturated alicyclic hydrocarbons, and aryl substituted aliphatic and alicyclic hydrocarbons.

3. A process according to claim 2 wherein said aliphatic hydrocarbon compounds are selected from methane, ethane, propane, butane, heptane, pentane, hexane, octane, isobutane, isohexane, isooctane, 1-pentene, 1-hexene and mixtures thereof.

4. A process according to claim 2 wherein said alicyclic hydrocarbon compounds are selected from cyclobutane, cycloheptane, cycloheptene, cyclohexane, cyclohexene, and mixtures thereof.

5. A process according to claim 2 wherein said aryl substituted aliphatic and alicyclic hydrocarbon compounds are selected from toluene, oxylene, mesitylene, durene, cumene and mixtures thereof.

6. A process according to claim 2 wherein said aliphatic and alicyclic substituted aromatic hydrocarbon compounds are selected from aromatic ring hydrocarbons having at least one aliphatic or alicyclic hydrocarbon radical substituent on the aromatic ring.

7. A process according to claim 6 wherein said aromatic hydrocarbon compounds are selected from toluene, xylene, indan, tetralin and mixtures thereof.

8. A process according to claim 1 wherein B is selected from the group consisting of boron, aluminum, yttrium, lanthanum and mixtures thereof and C is selected from the group consisting of magnesium, calcium, barium, zinc and mixtures thereof.

9. A process according to claim 8 wherein x =0.05 to 0.15 and y =0.03 to 0.10.

10. A process according to claim 1 wherein B is selected from the group consisting of silicon, titanium, zirconium, hafnium and mixtures thereof and C is selected from the group consisting of boron, aluminum, yttrium, lanthanum and mixtures thereof.

11. A process according to claim 10 wherein x =0.05 to 0.15 and y =0.002 to 0.20.

12. A process according to claim 1 wherein said catalyst is a boron/alkali metal promoted metal oxide, said boron present in about 0.2 to about 20 mole percent, said alkali metal selected from the group consisting of lithium, sodium and potassium and present in about 0.1 to about 25 mole percent, and the balance said metal oxide selected from the group consisting of magnesium oxide, calcium oxide, zinc oxide, barium oxide and mixtures thereof.

13. A process according to claim 12 wherein said boron is present in about 0.4 to about 2 mole percent.

14. A process according to claim 12 wherein said alkali metal is present in about 0.5 to about 8 mole percent.

15. A process according to claim 12 wherein said alkali metal is selected from the group consisting of lithium, sodium, potassium and mixtures thereof.

16. A process according to claim 12 wherein said alkali metal is lithium.

17. A process according to claim 12 wherein said metal oxide is selected from the group consisting of magnesium oxide, calcium oxide, zinc oxide, barium oxide and mixtures thereof.

18. A process according to claim 12 wherein said metal oxide is magnesium oxide.

19. A process according to claim 12 wherein said process is carried out at a temperature of about 300° to about 1100° C.

20. A process according to claim 12 wherein said process is carried out at a temperature of about 600o to about 900° C.

21. A process according to claim 12 wherein said process is carried out at a pressure of about 1 to about 1515 psia.

22. A process according to claim 12 wherein said process is carried out at a pressure of about 1 to about 150 psia.

23. A process according to claim 12 wherein the gas residence time is about 0.002 to about 0.00002 hr.

24. A process according to claim 12 wherein the gas residence time is about 0.0005 to about 0.0001 hr.

25. A process according to claim 12 wherein said compound selected from aliphatic hydrocarbon compounds, alicyclic hydrocarbon compounds and mixtures thereof is fed to a reaction zone in about 50 to about 90 mole percent; said compound selected from aliphatic substituted aromatic hydrocarbon compounds, alicyclic substituted aromatic hydrocarbon compounds and mixtures thereof is fed to said reaction zone in about 2 to about 40 mole percent; and said oxygen is fed to said reaction zone in about 2 to about 20 mole percent.

26. A process according to claim 12 wherein said compound selected from aliphatic hydrocarbon compounds, alicyclic hydrocarbon compounds and mixtures thereof is fed to a reaction zone in about 75 to about 85 mole percent; said compound selected from aliphatic substituted aromatic hydrocarbon compounds, alicyclic substituted aromatic hydrocarbon compounds and mixtures thereof is fed to said reaction zone in about 5 to about 15 mole percent; and said oxygen is fed to said reaction zone in about 5 to about 12 mole percent.

27. A process according to claim 1 wherein said process is carried out at a temperature of about 300° to about 1100° C.

28. A process according to claim 1 wherein said process is carried out at a temperature of about 600° to about 900° C.

29. A process according to claim 1 wherein said process is carried out at a pressure of about 1 to about 1515 psia.

30. A process according to claim 1 wherein said process is carried out at a pressure of about 1 to about 150 psia.

31. A process according to claim 1 wherein the gas residence time is about 0.002 to about 0.00002 hr.

32. A process according to claim 1 wherein the gas residence time is about 0.0005 to about 0.0001 hr.

33. A process according to claim 1 wherein said compound selected from aliphatic hydrocarbon compounds, alicyclic hydrocarbon compounds and mixtures thereof is fed to a reaction zone in about 50 to about 90 mole percent; said compound selected from aliphatic substituted aromatic hydrocarbon compounds, alicyclic substituted aromatic hydrocarbon compounds and mixtures thereof is fed to said reaction zone in about 2 to about 40 mole percent; and said oxygen is fed to said reaction zone in about 2 to about 20 mole percent.

34. A process according to claim 1 wherein said compound selected from aliphatic hydrocarbon compounds, alicyclic hydrocarbon compounds and mixtures thereof is fed to a reaction zone in about 75 to about 85 mole percent; said compound selected from aliphatic substituted aromatic hydrocarbon compounds, alicyclic substituted aromatic hydrocarbon compounds and mixtures thereof is fed to said reaction zone in about 5 to about 15 mole percent; and said oxygen is fed to said reaction zone in about 5 to about 12 mole percent.

35. A process according to claim 1 wherein said process is carried out at a temperature of about 300° to about 1100° C., said pressure is about 1 to about 1515 psia, the gas residence time is about 0.002 to about 0.0002 hr, and said compound is selected from aliphatic hydrocarbon compounds, alicyclic hydrocarbon compounds and mixtures thereof is fed to a reaction zone in about 50 to about 90 mole percent; said compound selected from aliphatic substituted aromatic hydrocarbon compounds, alicyclic substituted aromatic hydrocarbon compounds and mixtures thereof fed to said reaction zone in about 2 to about 40 mole percent; and said oxygen is fed to said reaction zone in about 2 to about 20 mole percent.

* * * * *